United States Patent
Vu et al.

(10) Patent No.: US 11,207,057 B1
(45) Date of Patent: Dec. 28, 2021

(54) NASOPHARYNGEAL SAMPLE COLLECTION DEVICES AND METHODS

(71) Applicant: Cyrano Medical, Inc., Tustin, CA (US)

(72) Inventors: Dac V. Vu, Tustin, CA (US); Minh Bui, Stanton, CA (US)

(73) Assignee: Cyrano Medical, Inc., Camden, DE (US)

( * ) Notice: Subject to any disclaimer, the term of this patent is extended or adjusted under 35 U.S.C. 154(b) by 0 days.

(21) Appl. No.: 17/246,436

(22) Filed: Apr. 30, 2021

Related U.S. Application Data

(60) Provisional application No. 63/113,708, filed on Nov. 13, 2020, provisional application No. 63/080,579, filed on Sep. 18, 2020, provisional application No. 63/071,010, filed on Aug. 27, 2020, provisional application No. 63/062,924, filed on Aug. 7, 2020.

(51) Int. Cl.
*A61B 10/00* (2006.01)
*A61M 1/00* (2006.01)
*A61M 3/02* (2006.01)

(52) U.S. Cl.
CPC ......... *A61B 10/0051* (2013.01); *A61M 1/774* (2021.05); *A61M 3/0262* (2013.01); *A61M 3/0279* (2013.01); *A61M 2202/0007* (2013.01); *A61M 2202/0014* (2013.01); *A61M 2210/0618* (2013.01)

(58) Field of Classification Search
CPC ............ A61B 10/0051; A61M 3/0262; A61M 3/0279; A61M 2210/0618; A61M 2202/0014; A61M 2202/0007; A61M 1/774
See application file for complete search history.

(56) References Cited

U.S. PATENT DOCUMENTS

| | | | |
|---|---|---|---|
| 128,257 A | 6/1872 | Snyder | |
| 1,502,163 A | 7/1924 | Sprague | |
| 1,856,811 A * | 5/1932 | Inaki | A61M 3/0262 604/38 |
| 3,502,078 A | 3/1970 | Hill et al. | |
| 3,785,366 A | 1/1974 | Davis | |
| 4,029,095 A | 6/1977 | Pena | |

(Continued)

FOREIGN PATENT DOCUMENTS

| | | |
|---|---|---|
| EP | 1584340 A1 | 10/2005 |
| EP | 2389918 A1 | 11/2011 |

(Continued)

*Primary Examiner* — Sean P Dougherty
(74) *Attorney, Agent, or Firm* — Rollins IP; John F. Rollins

(57) ABSTRACT

Kits, devices, systems and related methods for obtaining a nasopharyngeal sample utilize a rinsing fluid supply component and a collecting component, which may be used as separate modules or integrated with a housing to form a handheld unit that may be operated with a single hand. The dispensing component may include a flexible reservoir pump containing a supply of rinsing fluid, and a first nostril interface adapted to engage a first nostril of a patient and guide a stream of rinsing fluid into the patient's nasal cavity. The collecting component may include a collection container and a second nostril interface adapted to engage a second nostril of a patient and collect effluent. An absorbent shield may be arranged on the integrated unit to absorb stray fluid.

19 Claims, 18 Drawing Sheets

(56) References Cited

U.S. PATENT DOCUMENTS

| | | | |
|---|---|---|---|
| 4,709,705 | A | 12/1987 | Truglio |
| 5,116,311 | A | 5/1992 | Lofstedt |
| 5,252,458 | A | 10/1993 | Liav et al. |
| 5,643,202 | A | 7/1997 | Gravenstein et al. |
| 5,788,683 | A | 8/1998 | Martin |
| 6,443,152 | B1 | 9/2002 | Lockhart et al. |
| 6,520,384 | B2 | 2/2003 | Mehta |
| 6,561,188 | B1 * | 5/2003 | Ellis ............ A61M 3/0262 128/203.22 |
| 6,589,219 | B1 * | 7/2003 | Shibuya ............ A61G 7/0503 604/319 |
| 6,669,059 | B2 | 12/2003 | Mehta |
| 6,688,497 | B2 | 2/2004 | Mehta |
| 6,736,792 | B1 | 5/2004 | Liu |
| 7,143,763 | B2 | 12/2006 | Abate |
| 7,629,114 | B2 | 12/2009 | Tong et al. |
| 7,927,548 | B2 | 4/2011 | Slowey et al. |
| 7,981,077 | B2 | 7/2011 | Hoke et al. |
| 8,092,434 | B2 | 1/2012 | Harlan et al. |
| 8,556,089 | B2 | 10/2013 | Kalayci et al. |
| 9,427,504 | B2 | 8/2016 | Newman |
| 9,625,451 | B2 | 4/2017 | Izuhara et al. |
| 9,683,256 | B2 | 6/2017 | Fischer et al. |
| 9,750,856 | B2 | 9/2017 | Baker et al. |
| 9,764,080 | B2 | 9/2017 | Mehta |
| 9,884,147 | B2 | 2/2018 | Azeez |
| 9,993,584 | B2 | 6/2018 | Mehta et al. |
| 9,999,567 | B2 | 6/2018 | Hoke et al. |
| 10,080,857 | B2 | 9/2018 | Sislian et al. |
| 10,206,927 | B2 | 2/2019 | Henkin |
| 10,226,554 | B2 | 3/2019 | Baker et al. |
| 10,248,765 | B1 | 4/2019 | Holmes et al. |
| 10,265,462 | B2 | 4/2019 | Layer et al. |
| 10,342,903 | B2 | 7/2019 | Baker et al. |
| 10,383,984 | B2 | 8/2019 | Hoke et al. |
| 10,407,733 | B2 | 9/2019 | Ng |
| 10,478,547 | B2 | 11/2019 | Rubin et al. |
| 10,620,221 | B2 | 4/2020 | Szymanski et al. |
| 10,767,215 | B2 | 9/2020 | Birnboim et al. |
| 10,814,058 | B2 | 10/2020 | Yang et al. |
| 2005/0065470 | A1 | 3/2005 | Reed et al. |
| 2006/0045605 | A1 | 3/2006 | Deans et al. |
| 2006/0249161 | A1 | 11/2006 | Waters et al. |
| 2008/0221507 | A1 * | 9/2008 | Hoke ............ A61M 1/70 604/28 |
| 2009/0202665 | A1 | 8/2009 | Javer et al. |
| 2009/0221987 | A1 | 9/2009 | Mansur |
| 2009/0247941 | A1 * | 10/2009 | Lu ............ A61M 3/0262 604/73 |
| 2009/0275015 | A1 | 11/2009 | Bonner |
| 2009/0281454 | A1 | 11/2009 | Baker et al. |
| 2010/0152653 | A1 | 6/2010 | Hoke et al. |
| 2013/0060235 | A1 | 3/2013 | Liu |
| 2014/0171794 | A1 | 6/2014 | Liu |
| 2015/0164398 | A1 | 6/2015 | Ko et al. |
| 2016/0151052 | A1 | 6/2016 | Balwani |
| 2016/0250408 | A1 | 9/2016 | Djupesland |
| 2016/0339188 | A1 * | 11/2016 | Flickinger ............ A61M 15/08 |
| 2017/0028144 | A1 * | 2/2017 | Flickinger ............ A61M 11/06 |
| 2018/0031550 | A1 | 2/2018 | Rubin et al. |
| 2018/0126063 | A1 | 5/2018 | Mehta |
| 2020/0297915 | A1 | 9/2020 | Rubin et al. |

FOREIGN PATENT DOCUMENTS

| | | | | |
|---|---|---|---|---|
| FR | 3016125 | A1 * | 1/2014 | ............ A61H 35/04 |
| FR | 3016125 | B1 | 10/2017 | |
| FR | 3092991 | * | 8/2020 | ............ A61H 35/04 |
| FR | 3092991 | A1 | 8/2020 | |
| GB | 178630 | A | 4/1922 | |
| KR | 2023838 | B1 * | 3/2018 | ......... A61M 3/0262 |

\* cited by examiner

US 11,207,057 B1

NASOPHARYNGEAL SAMPLE COLLECTION DEVICES AND METHODS

PRIORITY CLAIM AND RELATED APPLICATIONS

This application claims priority to U.S. provisional application Ser. No. 63/113,708 titled NASAL TEST KIT, filed on Nov. 13, 2020, the subject matter of which is incorporated herein in its entirety.

FIELD

The present disclosure relates to apparatus, systems, devices and methods for collecting test and diagnostic samples from a patient's body. More specifically, the present disclosure relates to apparatus, systems, devices and methods for collection of nasopharyngeal samples, including nasopharyngeal fluids from a patient body.

BACKGROUND

There is an urgent need in the art for kits, devices, systems and methods that facilitate safe, cost-effective and widespread testing for pathogens, particularly viruses. The onset and persistence of the global COVID-19 pandemic has amplified this need and urgency.

Testing of patient nasopharyngeal fluids can be used for the detection and diagnosis of patient infection from pathogens, particularly viruses. One known approach is the extraction of nasopharyngeal fluid by insertion of a swab through a patient nostril and into the patient's nasopharynx. However, such methods are viewed as quite intrusive and are uncomfortable, even painful, and can be particularly repulsive to patients, particularly pediatric patients.

Development of feasible and practical solutions for obtaining nasopharyngeal fluids are characterized by a number of challenges. One challenge is to provide kits, devices and associated methods that facilitate less intrusive and/or more comfortable extraction of nasopharyngeal samples compared to know devices, methods and the prior art. Another challenge is to provide kits and devices that are capable of rapid, low-cost production and which thereby facilitate deployment on a mass, even global, scale, as well as facilitate single use and disposability. Still another challenge is to provide devices that are easy to use and which support self-administered testing and home use. Yet another challenge is to provide kits and devices that facilitate easy capture, transport and delivery of nasopharyngeal fluid sample directly to standard test tube to reduce laborious sample transfer and sample extraction processes in high volume sample processing laboratories. For pathogens that may be transmitted by aerosolization, or that have high transmissibility outside of human hosts, another challenge is to provide kits, devices and methods that facilitate control and containment of fluids and reduce the risk of dripp age and aerosolization. There is thus a need for advances in the art that overcome the above challenges and others.

SUMMARY

In accordance with some aspects, the present disclosure provides kits, devices, systems and related methods for obtaining a nasopharyngeal sample using a rinsing fluid supply component comprising a flexible reservoir pump having an interior for containing a supply of rinsing fluid, a rinsing fluid delivery conduit extending from the reservoir and having a delivery conduit flow passage therein; and a first nostril interface disposed on the delivery conduit and adapted to engage a first nostril of a patient, and a collecting component, the collecting component comprising a collection container interface for receiving a collection container; a collection conduit extending to the collection interface; and a second nostril interface disposed on the collection conduit and adapted to engage a second nostril of a patient. A stream of rinsing fluid may be dispensed into the patient's nasal cavity with a simple motion of a single hand to flush a nasopharyngeal sample into the collecting component.

According to another aspect, the kit may include a housing for supporting the rinsing fluid supply component and the rinsing fluid collecting component, wherein the rinsing fluid supply component is adapted to be secured to the housing and the rinsing fluid supply component is adapted to be secured to the housing. According to a further aspect, the housing may comprise a flexible bridge that is adapted to flex to permit adjustment of the relative positions of the first and second nostril interfaces. According to a further aspect, at least one of the first and second nostril interfaces may comprise an absorbent foam adapted to absorb fluid. According to another aspect, the flexible reservoir is adapted to resiliently revert to a resting shape so as to permit a user to utilize the flexible reservoir as a vacuum source. According to another aspect, the collection container interface is adapted to receive a standard autosampler vial. According to another aspect, at least one of the first and second nostril interfaces comprise a tapered plug of absorbent foam. According to another aspect, the delivery conduit comprises a drop tube that extends to a bottom portion of the reservoir. According to another aspect, the collecting component includes a one-way valve. According to another aspect, at least one of the rinsing fluid delivery conduit and collection conduit comprise a flexible section adapted to permit adjustment of the relative positions of the first and second nostril interfaces. According to another aspect, the collecting component includes at least one venting passage. According to another aspect, the first nostril interface includes at least one collection reservoir. According to another aspect, the second nostril interface includes at least one collection passage. According to another aspect, the kit may comprise a bridge connecting the dispensing component and the collecting component, wherein the flexible reservoir pump and collection container interface are formed integrally with the bridge as a unitary piece. According to another aspect, the kit may comprise an absorbent shield having a horizontal portion and a vertical portion for absorbing stray fluid.

According to another aspect, there is provided a method of collecting a sample of nasopharyngeal fluid comprising providing a rinsing fluid supply component comprising a flexible bulb-shaped reservoir having an interior for containing a supply of rinsing fluid; a rinsing fluid delivery conduit extending from the reservoir and having a delivery conduit flow passage therein; and a first nostril interface disposed on the delivery conduit and adapted to engage a first nostril of a patient, providing a rinsing fluid collecting component adapted to be secured to the housing the rinsing fluid collecting component comprising: a collection container interface for receiving a collection container; a collection conduit extending to the collection interface; and a second nostril interface disposed on the collection conduit and adapted to engage a second nostril of a patient, supplying rinsing fluid from the rinsing fluid supply component through the first nostril interface and into a first nostril and into a nasopharyngeal cavity of a patient; and collecting rinsing fluid from the nasopharyngeal cavity of the patient with the rinsing fluid collecting component. According to another aspect, a device for collecting a sample of nasopharyngeal fluid may comprise a rinsing fluid supply component comprising a flexible reservoir pump having an interior for containing a supply of rinsing fluid; a rinsing fluid delivery conduit extending from the reservoir and having a delivery conduit flow passage therein; and a first nostril interface disposed on the delivery conduit and adapted to engage a first nostril of a patient; a collecting component, the collecting component comprising: a collection container interface for receiving a collection container; a collection conduit extending to the collection interface; and a second nostril interface disposed on the collection conduit and adapted to engage a second nostril of a patient; and a housing connecting the rinsing fluid supply component and the collecting component.

BRIEF DESCRIPTION OF THE DRAWINGS

The features described in this disclosure are set forth with particularity in the appended claims. These features and attendant advantages will become apparent from consideration of the following detailed description, taken in conjunction with the accompanying drawings. One or more embodiments are now described, by way of example, with reference to the accompanying drawings wherein like reference numerals represent like elements. All examples illustrated and described are according to aspects of the disclosure, unless otherwise noted.

FIGS. 1-10 illustrate a first example device according to aspects of the disclosure, in which: FIG. 1 is a perspective left rear view of an assembled device;

FIG. 2 is a perspective left front view of the device of FIG. 1;

FIG. 3 is an exploded isometric left rear view of the example device of FIG. 1;

FIG. 4 is a top view of the device of FIG. 1;

FIG. 5 is a bottom view of a dispensing component nostril interface cone of the example device of FIG. 1;

FIG. 6 is a bottom view of a collecting component nostril interface cone of the example device of FIG. 1;

FIG. 7 is a cross-section in plane 7-7 of FIG. 4;

FIG. 8 is a cross-section in plane 8-8 of FIG. 4;

FIG. 9 is a cross-section in plane 9-9 of FIG. 4; and

FIG. 10 is a cross-section in plane 10-10 of FIG. 4.

FIGS. 11-15 illustrate a second example device according to aspects of the disclosure, in which: FIG. 11 is a perspective left rear view of an assembled device;

FIG. 12 is an exploded, perspective view of the device in FIG. 11;

FIG. 13 is a top view of the device of FIG. 11;

FIG. 14 is a cross-section taken in plane 14-14 of FIG. 13; and

FIG. 15 is a detailed of the cross-section of FIG. 14, focused on the collecting component features.

FIGS. 17 and 18 illustrate a fourth example device according to aspects of the disclosure featuring components that are molded as a unitary piece, and featuring alternative dispensing component and collecting component features, in which: FIG. 17 is a perspective left rear view; and FIG. 18 is a cross section taken in plane 18-18 of FIG. 17.

FIGS. 19-21 illustrate another example nostril interface according to aspects of the disclosure in which:

FIG. 19 is a perspective view of a nostril interface according to another aspect of the disclosure;

FIG. 20 is a top view of the nostril interface of FIG. 19; and

FIG. 21 is a cutaway showing a cross-section of the nostril interface of FIG. 19.

DETAILED DESCRIPTION

Figure 1:
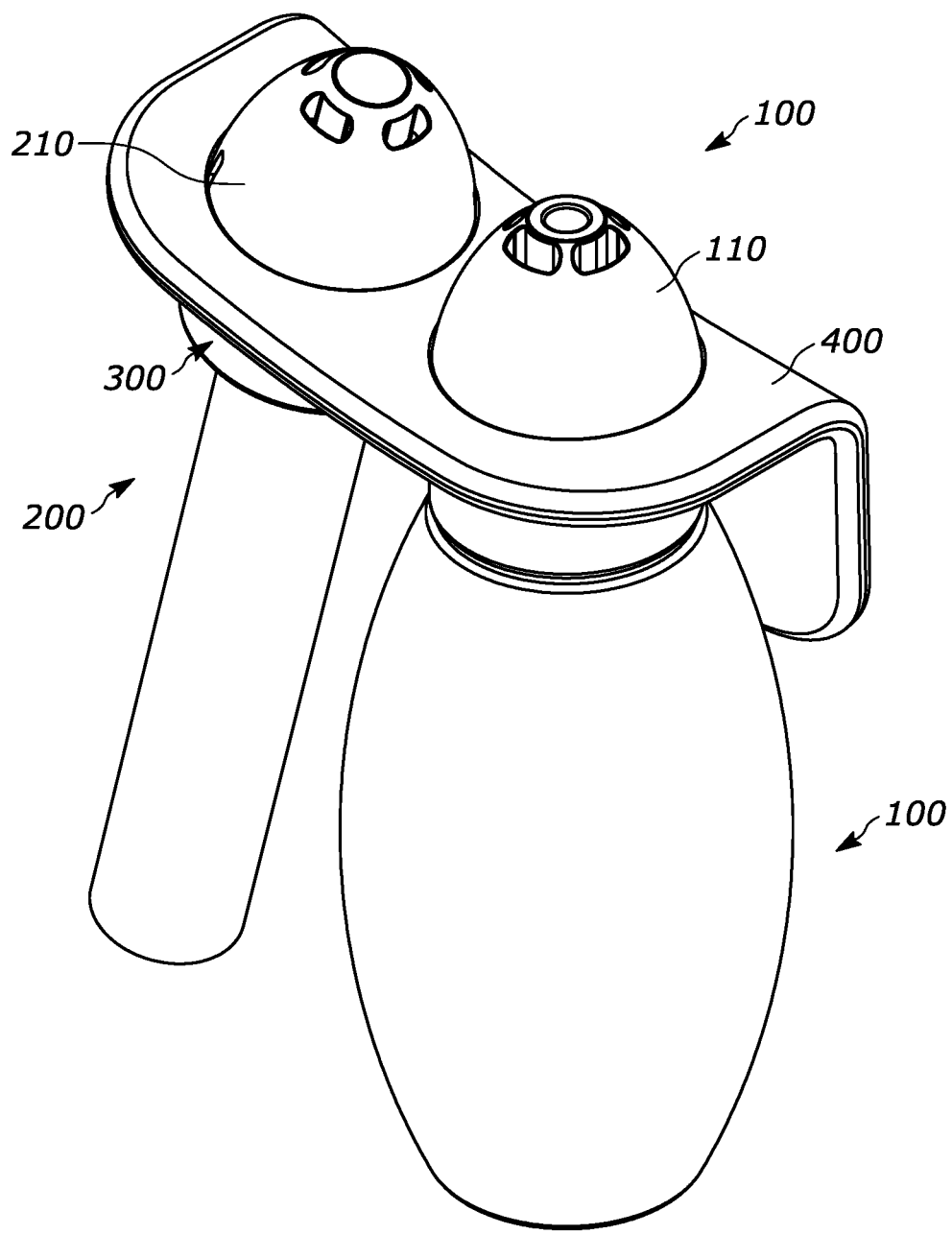

The present disclosure describes a number of embodiments of portable, nasopharyngeal testing kits, devices, systems and associated methods.

The term "adapted to," as used in the description and claims in reference to an element, component, or assembly, when preceding or used in reference to a function, requirement or result, should be understood to require that the element, component or assembly includes structure, which may operate, or be operated on, to achieve the function, requirement or result to which it refers.

The term "kit" as referred herein should be understood to apply to a set of components that may at some point in time be combined, connected or arranged to form an assembly, but which do not necessarily need to be in the combined, connected or arranged form.

The use of absolute terms, such as "must," "will," and the like, as well as specific quantities, is to be construed as being potentially applicable to one or more of such embodiments, but not necessarily to all such embodiments. As such, embodiments of the described systems, devices, and methods may omit, or include a modification of, one or more features or functionalities described in the context of such absolute terms.

Referring to FIGS. 1-10, a first example device according to aspects of the disclosure may include a rinsing fluid dispensing component 100, a collecting component 200, a housing or bridge 300 and an absorbent shield 400. Generally, and as will be further detailed herein, in operation and use, the device may be positioned and adjusted such that the dispensing component 100 and collecting component 200 interface with (i.e., are inserted into) respective nostrils of a patient. The dispensing component 100 provides for a user-controlled ejection and inflow of a stream of rinsing fluid (such as isotonic saline), for example, by a quick single operation of squeezing (i.e., by the patient or another user such as a physician) a flexible reservoir bulb, into a first patient nostril and into the patient's nasal cavity, where it may acquire nasopharyngeal fluid or other matter and create an outflow of effluent (i.e., a mixture of rinsing fluid and nasopharyngeal sample) from a second nostril of the patient. The collecting component 200 facilitates the controlled collection and containment of effluent outflow from the patient into a test vial, such as a standard autosampler test tube or vial for subsequent transport, testing and diagnosis. Housing 300 provides for a comfortable fit and support of both the dispensing component 100 and collecting component 200 to permit positioning and operation of the device using a single patient or user hand. Shield 400 provides for absorption of stray rinsing fluid or effluent, as well as patient comfort. The preceding is a general overview of operation. Further details of the kit, device, the constituent components and their function and associated methods will be described in subsequent parts of this description.

Referring particularly to FIGS. 1-3, 7 and 8, rinsing fluid dispensing component 100 may comprise a flexible, ergonomically advantageous bulb-shaped pump reservoir 102, which may be operated with a human hand, and which may define an interior volume for containing a supply of rinsing fluid. A threaded dispensing end 104, which may include a pump reservoir mouth 107 for permitting outflow of fluid, provides for attachment of a nostril interface, as will be described. A flexible outer wall 103 may be flexed inward to build pressure on the interior of the pump reservoir 102. Pump reservoir 102 may be provided with bottom support structure 106, which may include a recessed portion or dimple 108 and an annular support surface 109 for allowing the device to be supported on a horizontal surface for stabilization during use or storage. Pump reservoir 102 may be provided as a separate sealed package or unit containing a supply of rinsing fluid and may include a foil or other frangible membrane 111 fastened across the mouth 107 to secure contents and to ensure package safety and integrity.

In accordance with aspects of the instant disclosure, pump reservoir 102 and other subsequently described parts and components of the example kits and devices herein may be formed, molded (i.e., blow molded) or otherwise created from a flexible thermoplastic, which may be a safe, biocompatible, non-irritating, non-allergenic, or even a medical grade thermoplastic. which may have shape memory characteristics. Materials may include, polyethylene (low density or other), polypropylene, polyurethane, polycarbonate, polyetheretherketone or acrylonitrile butadiene styrene (ABS). Pump reservoir 102 may have a volume capacity of about 40 to 50 milliliters, which applicants have found provide suitable pressure, flow, cost and ergonomic characteristics. In accordance with aspects of the disclosure, the pump reservoir 102 and the material from which it is made may provide for the creation of a vacuum as the shape memory plastic returns to its resting state (i.e., undeformed, not squeezed, unpressurized state shown in the figures) after pressurization (squeezing). According to aspects of the disclosure, the vacuum created on the interior of pump reservoir 102 may be advantageous to provide additional control and containment of drippage or stray rinsing fluid or effluent during operation.

In accordance with aspects of the disclosure, the volume of rinsing fluid stored within the pump reservoir 102 may be selected to be an optimal amount to ensure that a single pumping action by the user may result in a thorough flushing of an average patient's nasopharyngeal passage and to ensure sufficient volume of effluent to facilitate thorough testing (i.e., immunoassay or otherwise). As will be recognized from the instant disclosure, adjustments can be made to these volumes and corresponding dimensions to provide for optimal performance and fluid management in pediatric or other applications.

Referring particularly to FIGS. 1-5, 7 and 8, according to aspects of the disclosure, a dispensing component nostril interface may be provided as a dispensing component nostril engagement tip, generally referenced 110, for engaging a patient nostril, and which defines an outer surface 114, which may be tapered, conical, spherical, or other shape that provides for a secure, substantially sealed engagement with a patient nostril, and a reduced diameter base 112 for securing the nostril engagement tip 110 to the housing 300. Nostril engagement tip 110 may incorporate or be made entirely of a suitable thermoplastic, silicone, or may incorporate or be made from absorbent foam. A dispensing port 116 is defined within the nostril engagement tip 110 and communicates with a dispensing passage 117 therethrough, which extends to a tapered drop tube mount 118 located in a threaded receptacle 105 for the threaded dispensing end of the reservoir pump 102. Tapered drop tube mount 118 may include a sharp lead edge for puncturing the foil seal on the pump reservoir 102. A drop tube 120 may optionally be secured to the nostril engagement tip 110 with a friction fit on the drop tube mount 118 and may define a drop tube passage 122, which communicates with the dispensing passage 117 and thus defining a passage from the lower interior of the pump reservoir 102 to the dispensing port 116. As will be recognized from the instant disclosure, drop tube 120 thus provides for ejection of rinsing fluid from the pump reservoir 102 while reducing the risk of air or other gas being introduced into the flow of rinsing fluid as it is dispensed. Pump reservoir 102 may be provided with a fill line indicator to indicate an optimal volume of rinsing fluid to be contained in the pump reservoir 102

Figure 7:
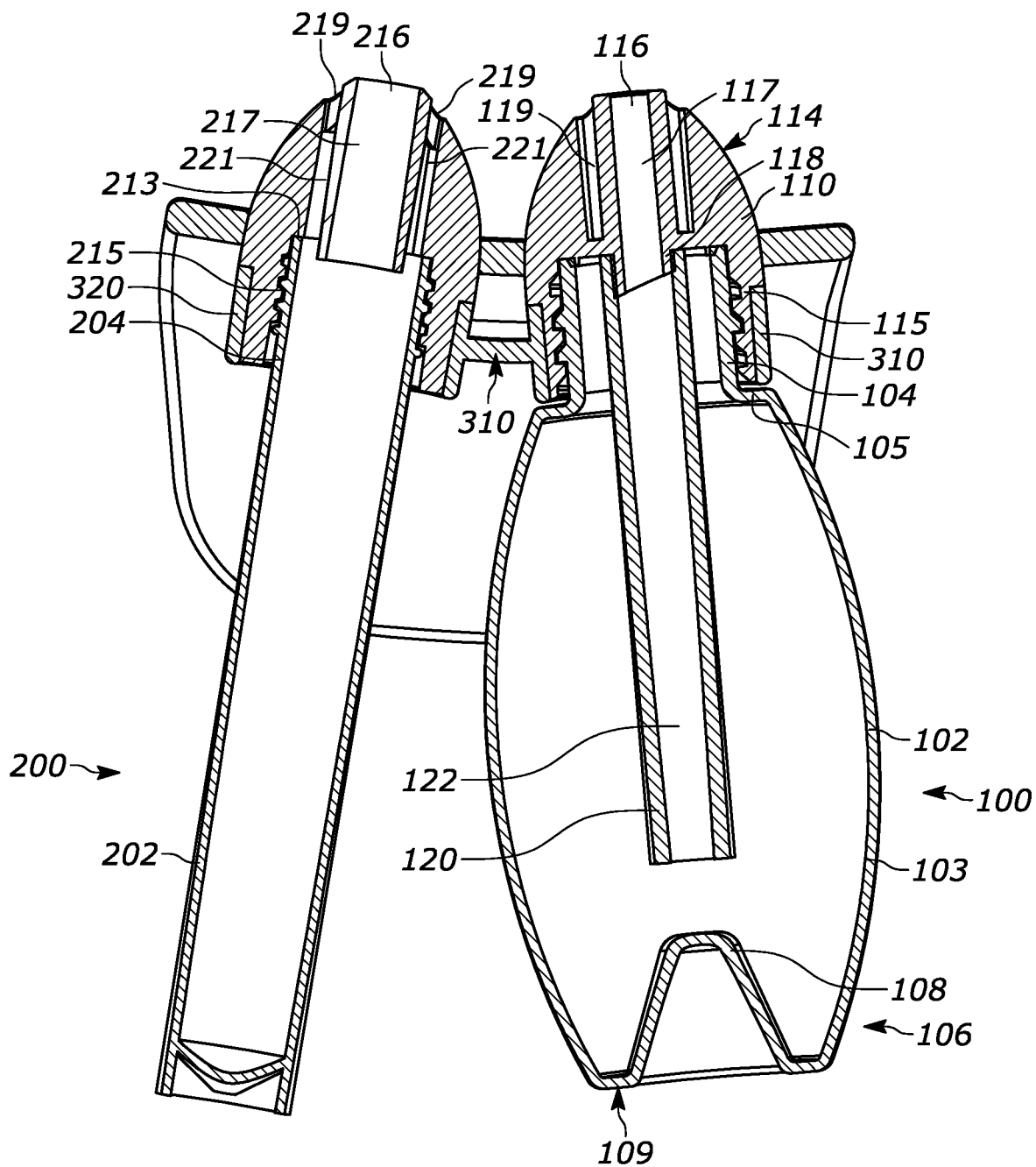
Figure 8:
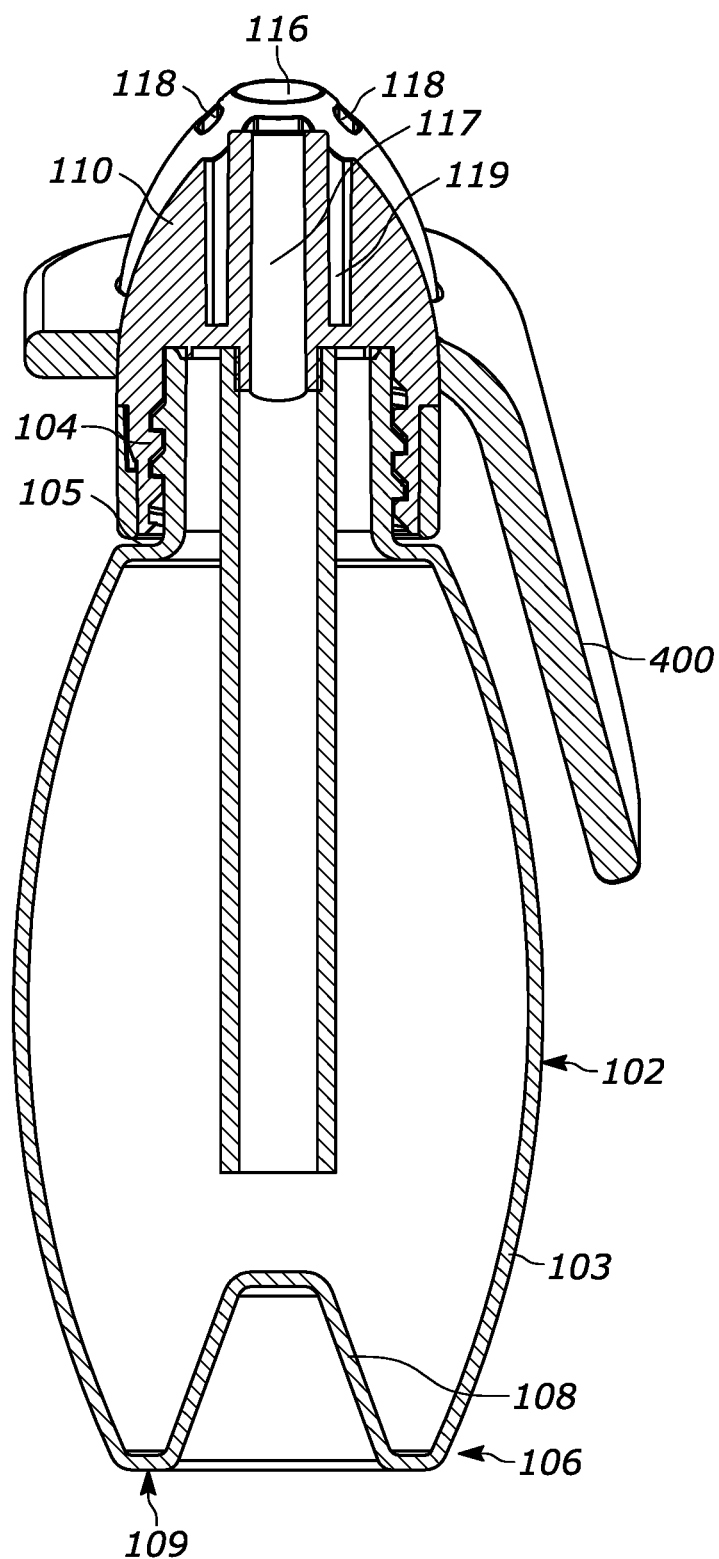
Figure 9:
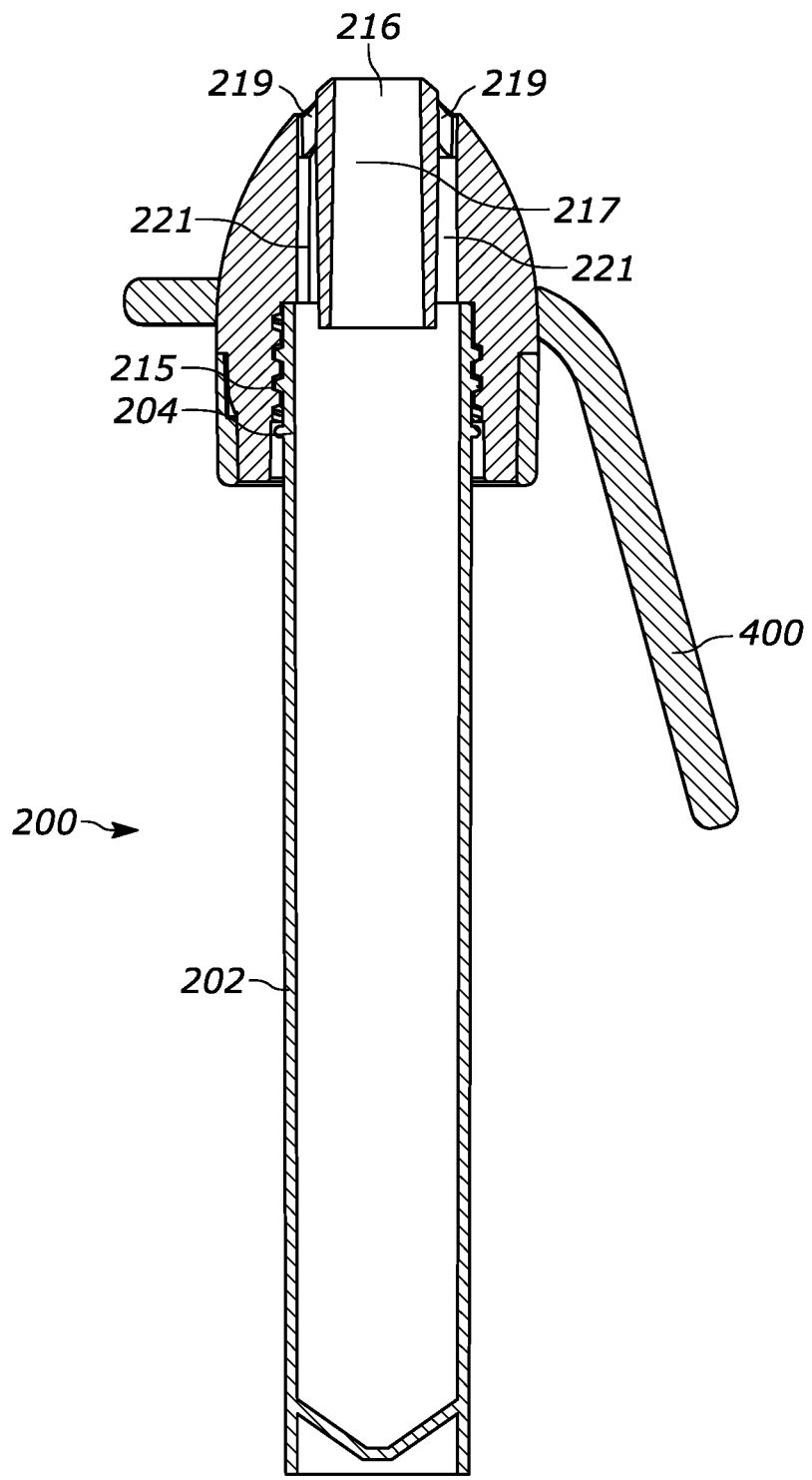

According to aspects of the disclosure, one or more (four, as illustrated) dispensing component collection reservoirs or wells 119 may be provided on the dispensing component nostril engagement tip 110 and arranged in a radial pattern around the dispensing port 116. These dispensing component collection reservoirs 119 may provide for the collection of excess or stray rinsing fluid or effluent during use of the device. FIG. 7 shows the dispensing component 100 in cross-section where the nostril engagement tip 110, with drop tube 120 secured thereto, is threaded onto the threaded dispensing end 104 of the pump reservoir 102. The threaded dispensing end 104 of the pump reservoir 102 may be provided with a removable, frangible or puncturable foil seal 111 and/or a threaded cap to ensure the safety and integrity of the stored rinsing fluid supply during shipping and prior to use.

According to further aspects of the disclosure, a sample collecting component 200 may include a sample collection tube 202 having a threaded open end 204. Sample collection tube 202 may be a standardized (i.e., 12×80 mm) autosampler test vial or micro test tube and have sufficient capacity to collect a 10 millilitre sample or microlitre of effluent, which is suitable for typical testing and diagnoses for many pathogens. A collecting component nostril interface may comprise a collecting component nostril engagement tip 210, which, similar to the dispensing component nostril engagement tip 110 described above, may be constructed using a suitable thermoplastic, which may be medical grade, and may include a tapered, spherical or conical nostril engagement surface and a reduced diameter base 212. A collection passage 217 extends from a collection port 216 through the collecting component nostril engagement tip to a threaded receptable 215 for the threaded end 204 of the sample collection tube 202. An annular collection tube seating/sealing surface 213 (FIG. 7) may be formed at an end of the threaded receptacle 215. In this regard, the threaded receptacle 215 and seating/sealing surface 213 may constitute a a collection tube interface, which, in this case is formed integrally with the collecting component nostril interface. As will be recognized from the instant disclosure, other forms of the collection tube interface are contemplated and made possible by the disclosure. For example, testing vial may be omit the threaded end and instead have an unthreaded end, which is friction fit within the collection tube interface on the collecting component 200.

According to a further aspect of the disclosure, the collecting component nostril engagement tip 210 may include a number of collection ports 219 arranged in a radial pattern around the collection port 216. Collection ports 219 provide for enhanced collection of effluent that may otherwise escape. Collection ports 219 communicate with respective collection passages 221 through the collecting component nostril engagement tip 210 and thereby permit the flow of collected effluents to the interior of collection tube 202.

Figure 10:
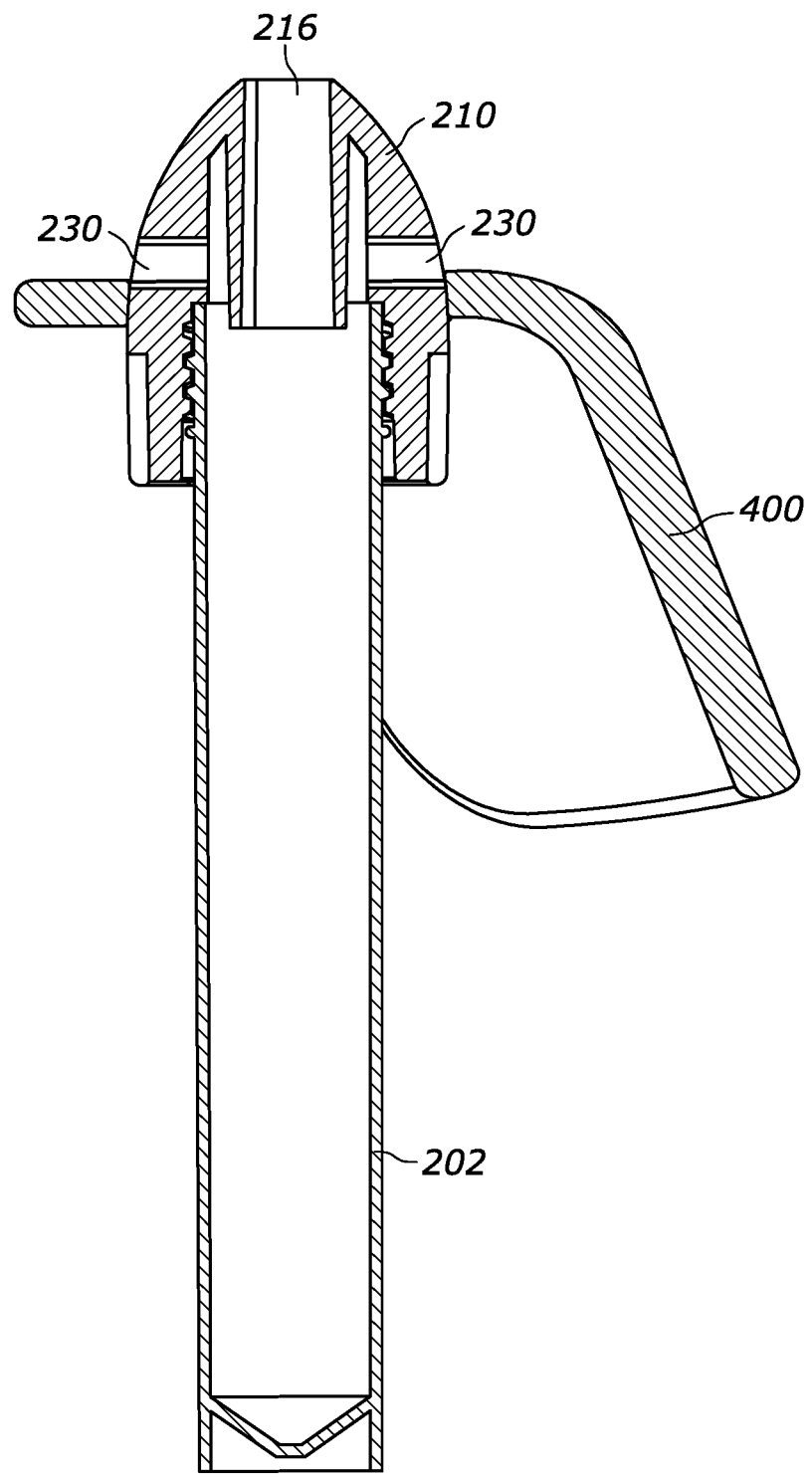
Figure 11:
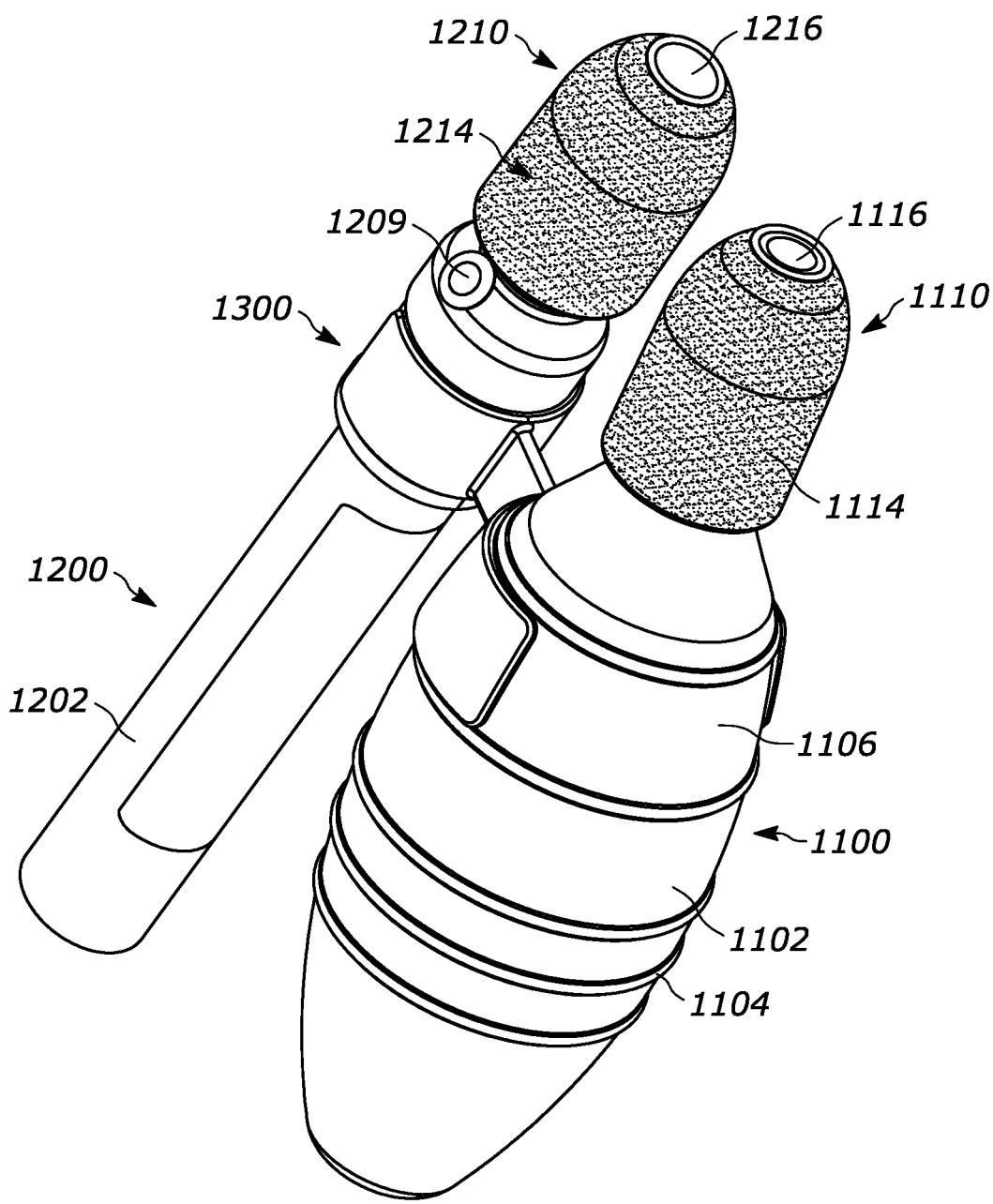
Figure 12:
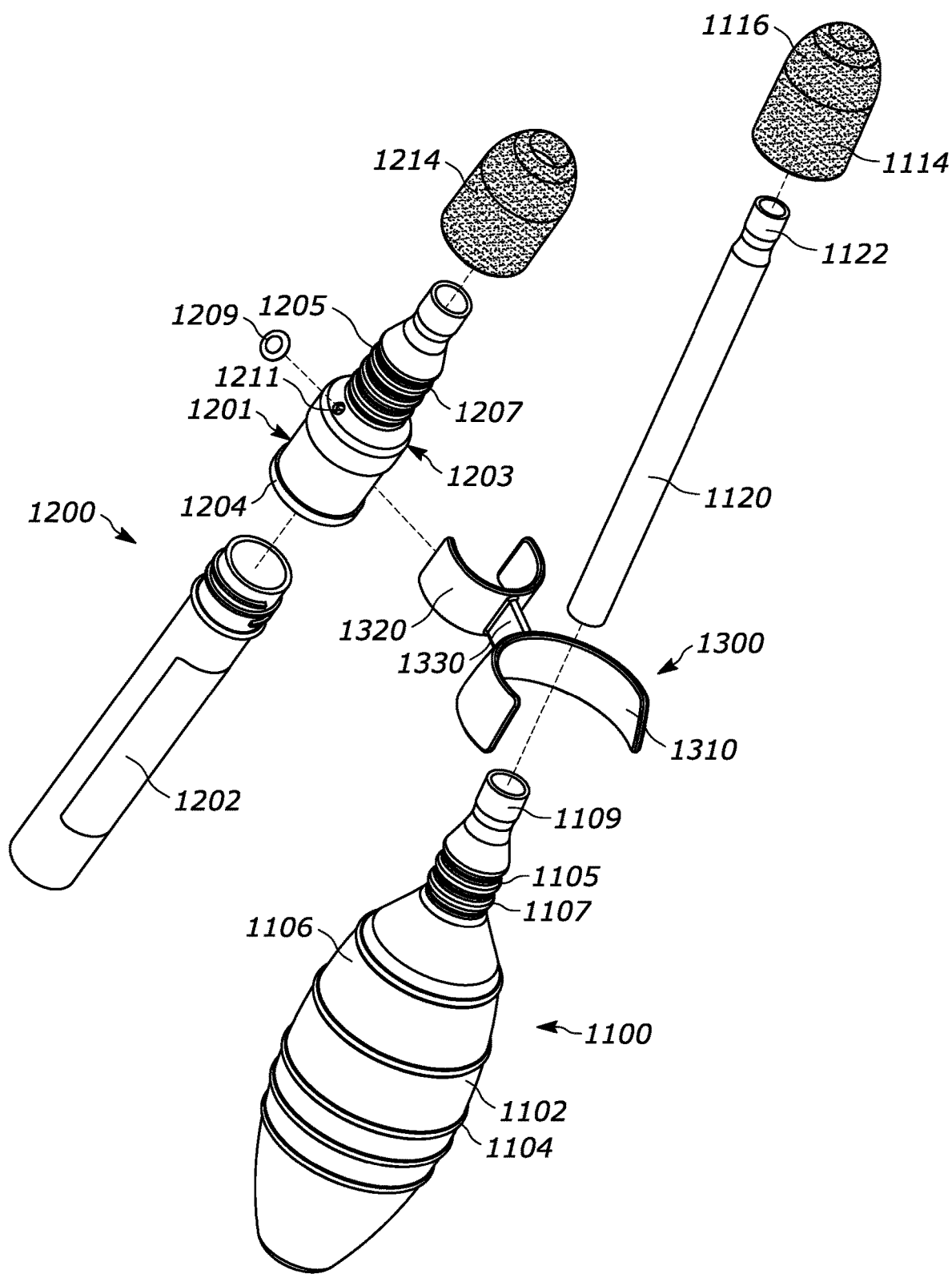
Figure 13:
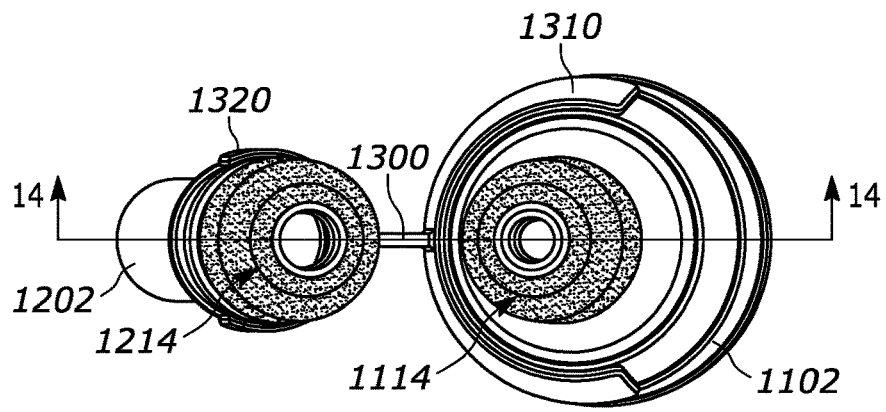
Figure 14:
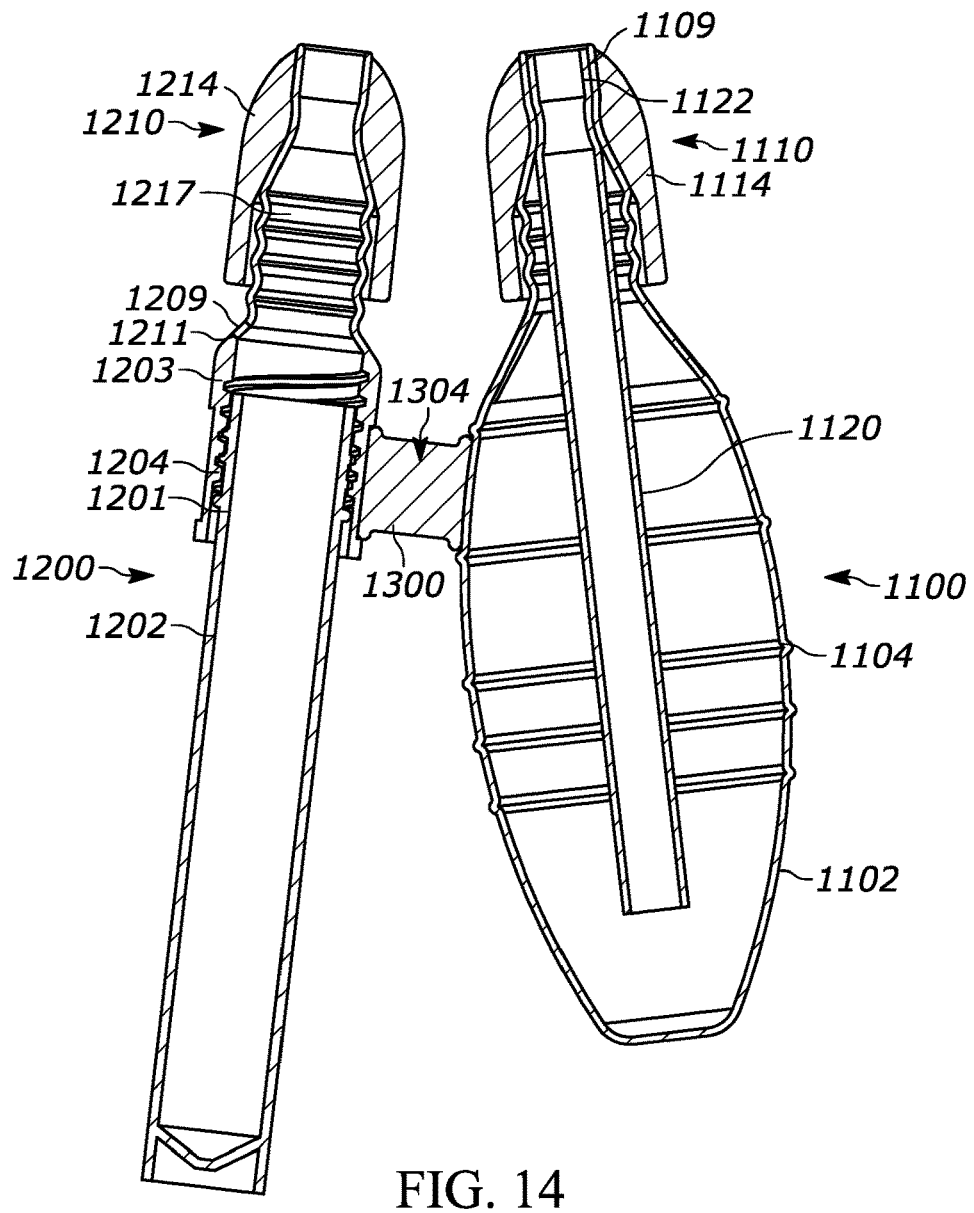
Figure 15:
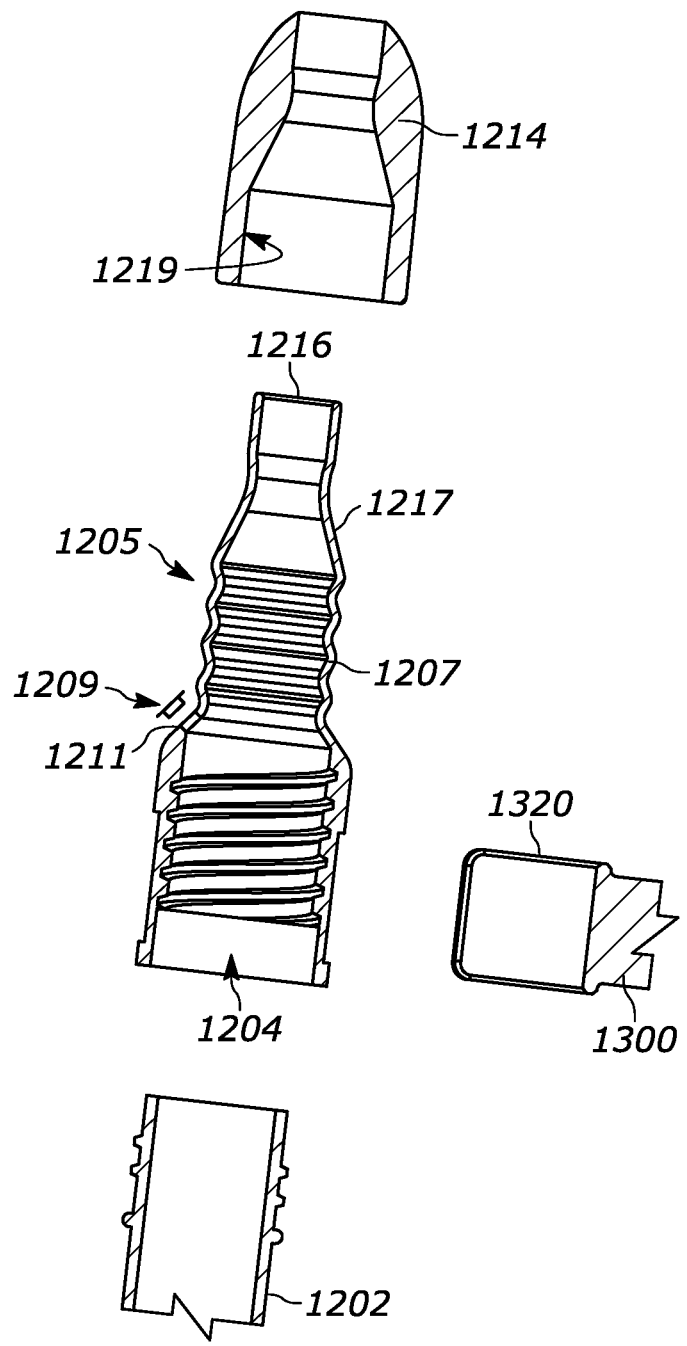

According to another aspect of the disclosure, as best shown in FIG. 10, the collecting component 200 may be provided with venting passages 230 in the nostril engagement tip 210. The venting passages 230 extend from respective venting ports 232 in the exterior surface of the provide for the venting of air from the collection tube 202, while preventing the passage of collected fluid from the collection tube 202. The venting passages 230 therefore prevent the buildup of pressure within the collection tube 202 as fluid (effluent) is collected, which pressure may otherwise interfere with the flow of collected effluent into the interior of collection tube 202. FIG. 7 shows the collecting component 200 in cross-section where the collecting component nostril engagement tip 210 is threaded onto the threaded dispensing end 204 of the collection tube 104.

According to an aspect of the disclosure, the dispensing component 100 and the collecting component 200 may be utilized as separate standalone components or modules in "modular" mode sampling methods. For example, a user may position the dispensing component 100 in one patient nostril using one hand and position the collecting component 200 in another patient nostril using another hand. Rinsing fluid may then be dispensed from the dispensing component 100 and effluent including nasopharyngeal matter collected in the collecting component 200 for subsequent testing. Alternatively, as described below, housing 300 may facilitate an "integrated" mode of use.

Figure 3:
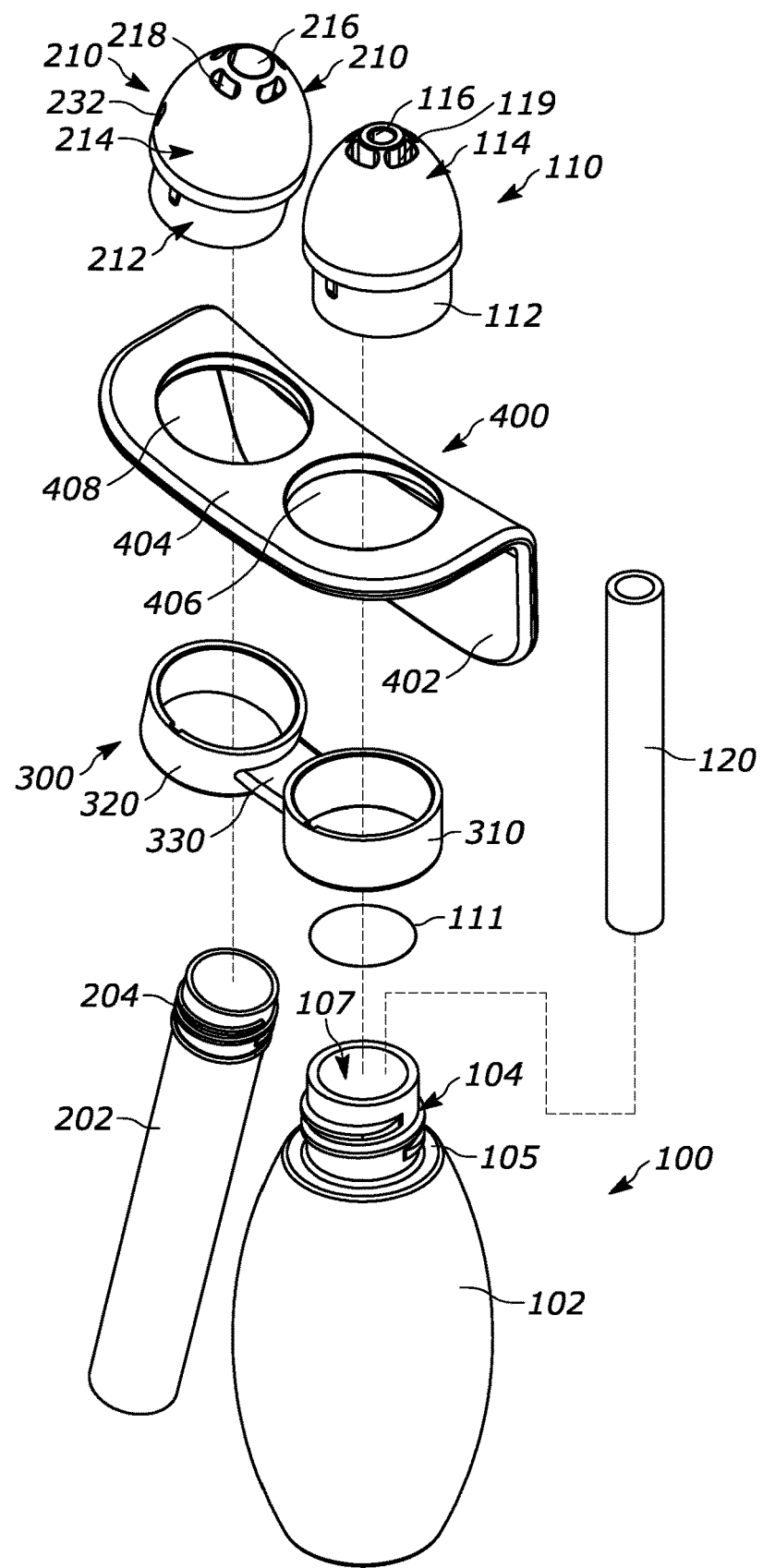
Figure 4:
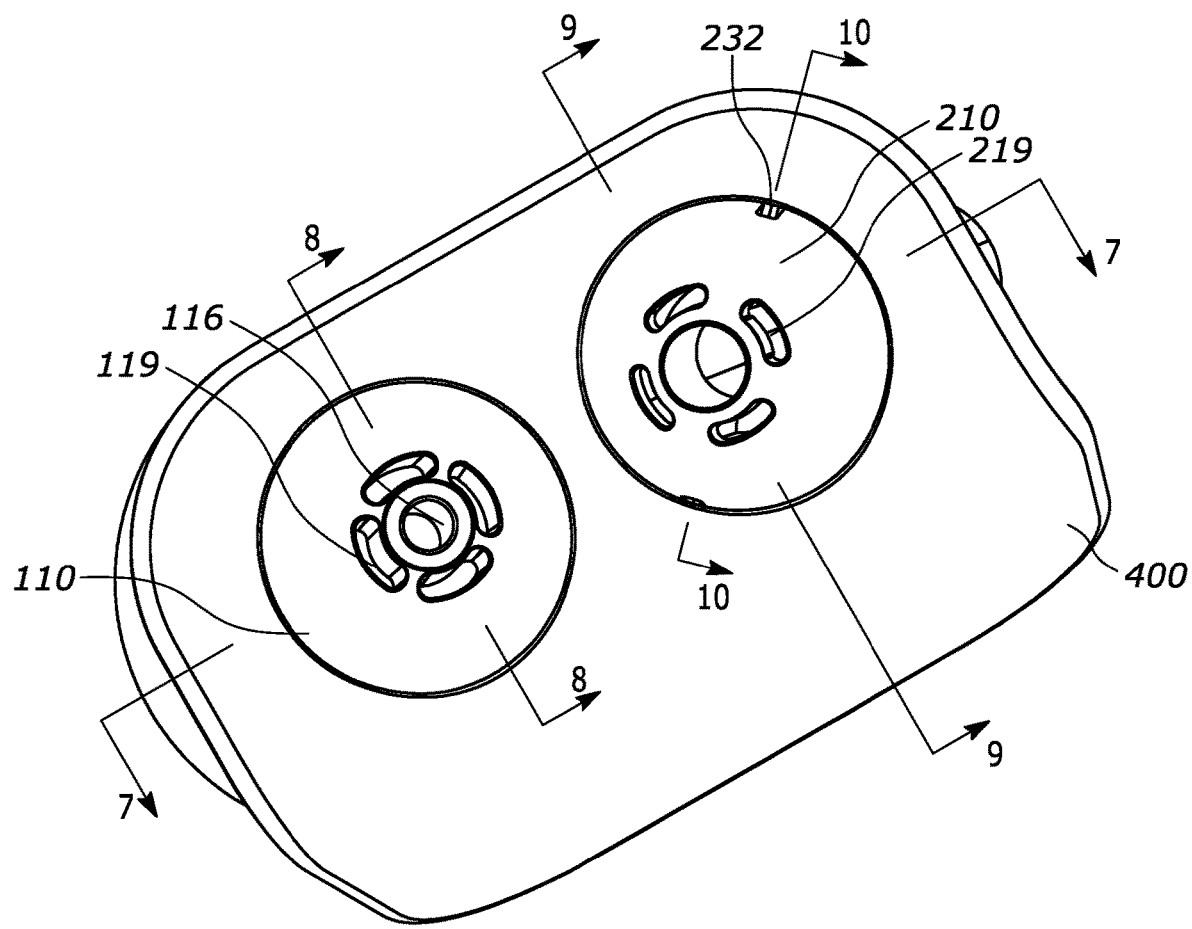
Figure 5:
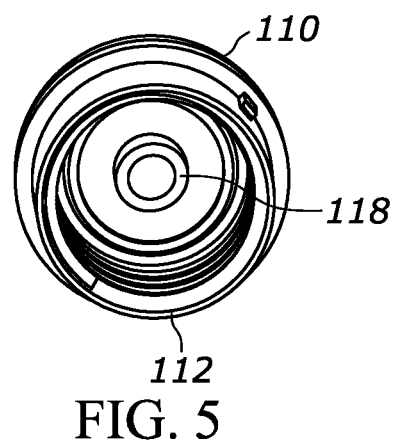
Figure 6:
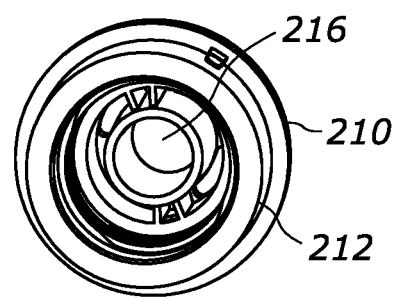

According to yet another aspect of the disclosure, a housing 300 may be utilized to secure the dispensing component 100 and collecting component 200 together as an integrated unit, which provide ease of use and operation with a single user hand. Referring particularly to FIGS. 3 and 7, housing 300 may include respective support rings 310 and 320 secured together by a flexible bridge or web 330. Support ring 310 surrounds the reduced diameter base 112 of the nostril engagement tip 110 and be frictionally engaged therewith (i.e., using a press fit) and further captured between the reduced diameter base 112 and the shoulder 105 of the pump reservoir 102 when the nostril engagement tip 110 is threaded onto the threaded portion 104 of the supply bulb 102. Support ring 320 may similarly engage the reduced diameter base 212 of the collecting component nostril cone 210, thereby retaining the collecting component 200 to the dispensing component 100. As will be recognized from the instant disclosure, bridge or web 330 may provide flexibility and adjustment with regard to the angle between the collecting component 200 and the dispensing component 100 (i.e., the angle between the respective axes of these components) to allow a user to adjust the relative position of the nostril interfaces as needed for particular patient characteristics.

Figure 2:
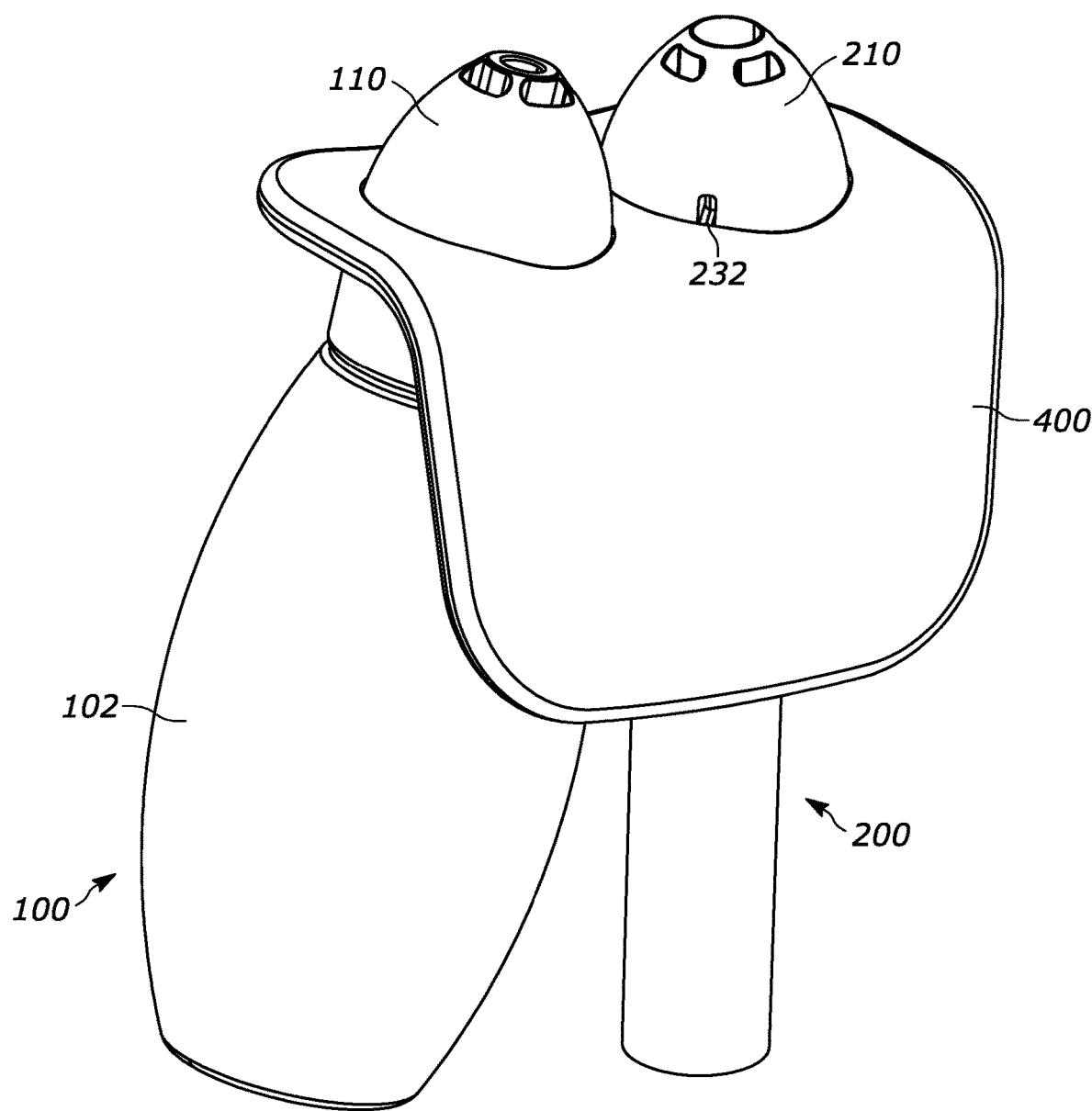

Shield, which may also be referred to as a bib or guard 400, may comprise an absorbent web, which may be formed as a substantially flat element and adapted to assume a generally L-shaped form when in an installed position as shown in FIGS. 1 and 2, with a horizontal web portion 404 and a vertical web portion 402. Horizontal web portion 404 may include respective circular cutouts 406 and 408, which receive the dispensing component nostril tip 120 and the collecting component nostril tip 210, respectively, to thereby secure the shield or guard 400 to those components and to the assembly. According to an aspect of the disclosure, shield 400 may be of a thickness and positioned to block the venting passages 230 such that any fluid that would otherwise escape through the venting passages 230 would be absorbed by the shield 400 and thus contained/controlled. Shield 400 may include or be formed from an absorbent cotton fabric or other material to provide for patient comfort and added control and absorption of stray effluent or rinsing fluid. Thus, various components of the device may work together to ensure control and containment of any drippage or stray fluid, reducing the risk of transmission of any pathogens and thus improving patient and public safety.

FIGS. 11-15 illustrate a second example device according to aspects of the disclosure. In this example, the dispensing component 1100 and collecting component are provided with respective nostril interfaces that incorporate flexible necks or extensions 1105 and 1205, as well as an alternative housing 1300 configuration.

Dispensing component 1100 may include a molded flexible bulb pump reservoir 1102, which may be formed from a memory thermoplastic, with a number of ribs 1104 on an external surface thereof. Ribs 1104 may enhance the tendency of the bulb to return to its resting state/shape and may define an alignment area 1106 to be engaged by the housing 1300. Bulb pump reservoir 1102 may extend upward to a flexible neck or extension 1105, which may include an undulating or serpentine or bellows portion 1107 which may provide for flexibility of the neck and provide for the neck to maintain a flexed shape. A drop tube 1120 may include an end 1122 which is sized to fit within an end 1109 of the neck 1105 to thereby retain the drop tube 1120 in the position shown in FIG. 12. As in the previous example, drop tube 1120 provides for dispensing of most of the rinsing fluid contained in the dispensing component 1100 to be dispensed while reducing the potential for air to be introduced into the dispensed fluid. Dispensing component 1100 may include a dispensing component nostril interface in the form of a soft absorbent foam nostril cone 1114 fitted onto the neck 1105. Cone 1114 may have a tapered surface 1116 for comfort and sealing engagement with various size patient nostrils.

Collecting component 1200 may include a molded collection tube interface 1203 having a threaded base 1204 for receiving a threaded end 1201 of the collection tube 1202. Threaded base 1204 may also include a recessed housing receiving and alignment area 1201 for receiving a gripping element 1320 of housing 1300. Base 1204 may extend upward to a flexible neck or extension 1205, which may include an undulating or serpentine or bellows portion 1207 which may provide for flexibility of the neck and provide for the neck to maintain a flexed shape. Flexible neck or extension 1205 further extends to a tapered portion 1217 and to collection port 1216. Neck or extension 1205 and tapered portion 1217 thus define a collection passage 1217 from the port 1216 to the interior of the collection tube 1202. A nostril cone 1214 is provided with an interior contoured surface 1219, which may be shaped complementarily to the neck 1205, for supporting the nostril cone 1214 thereon.

According to aspects of the disclosure, base 1204 may include a one-way valve 1209 for allowing the outflow of air from the interior of the collection tube 1202 as effluent is collected. One-way valve may include a button element secured within a valve receptacle and passage 1211 formed in the base 1204. Valve 1209 thus permits outflow from the interior of the collecting component 1200 while providing a seal to contain fluid on the interior of the collecting component 1200.

Housing 1300 includes opposed gripping elements 1310 and 1320 connected via a central extending web 1330 and engage respective receiving and alignment areas 1106 and 1201 on the dispensing component 1100 and collecting component 1200. Housing 1300 may thus support and integrate the dispensing component 1100 and collecting component 1200 for use of the kit in an integrated mode of operation. As with the previous example in FIGS. 1-11, and as will be recognized from the instant disclosure, the dispensing component 1100 and collecting component 1200 may be alternatively used as separate standalone modules in a modular mode of operation for obtaining the nasopharyngeal samples, for example, where each component is held in and operated by a respective hand of the user.

Figure 16:
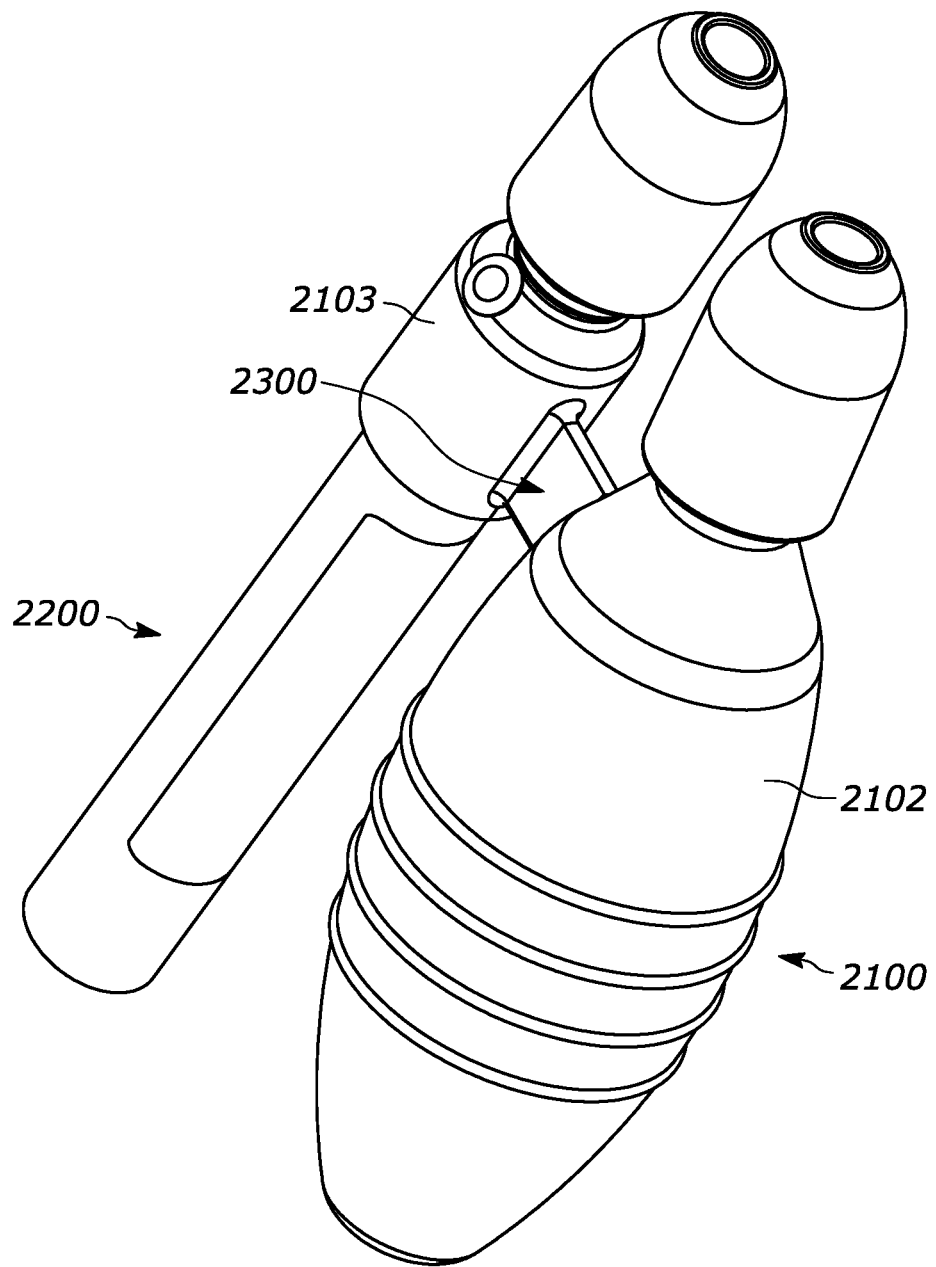
FIG. 16 illustrates a third example device according to aspects of the disclosure, featuring components that are molded as a unitary piece.

FIG. 16 shows a third example configuration, which is a variation on the example shown in FIGS. 12-15. In this example, elements of the dispensing component 2100 and collecting component 2200 are integrally molded together with a connecting bridge 2300.

Figure 17:
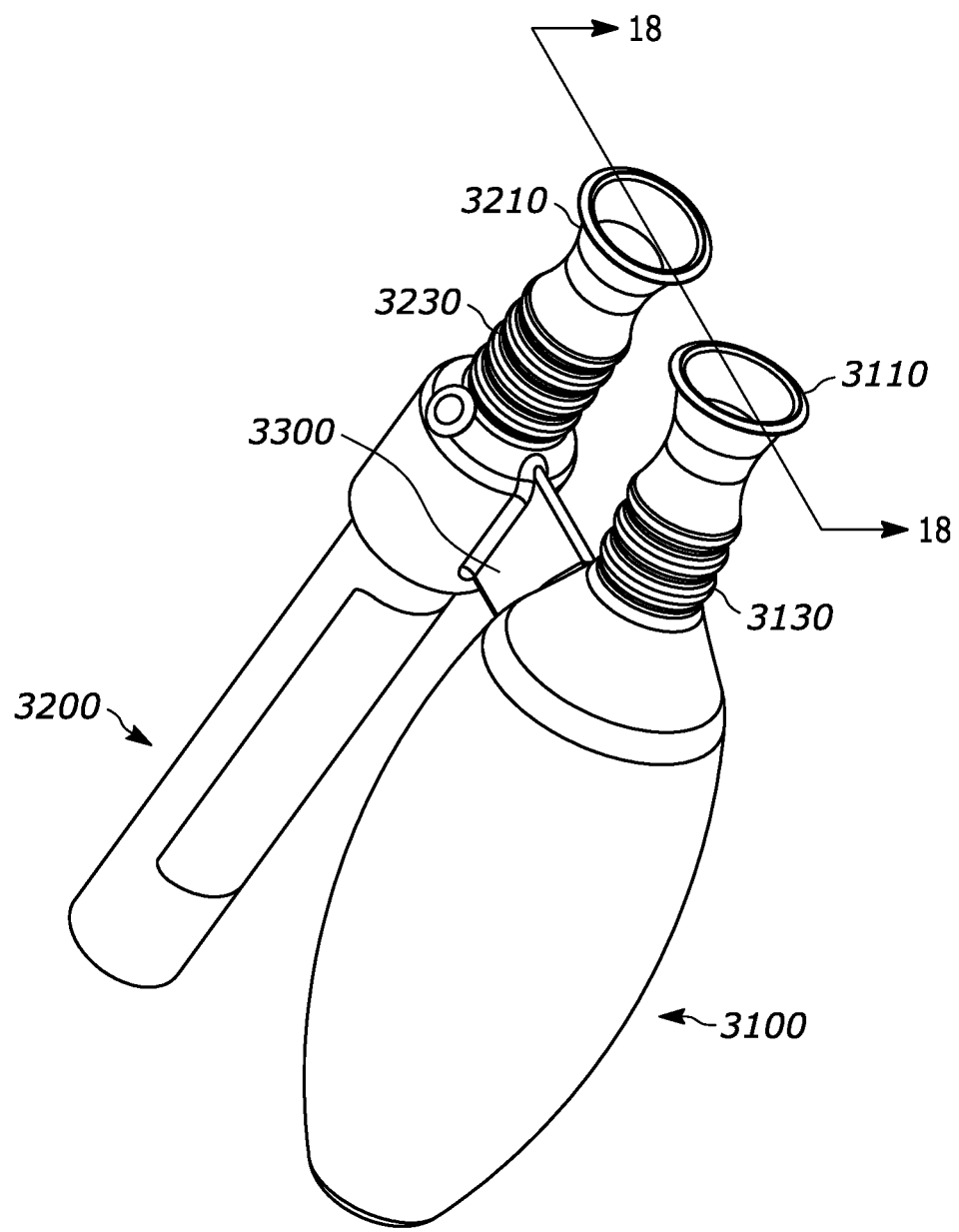
Figure 18:
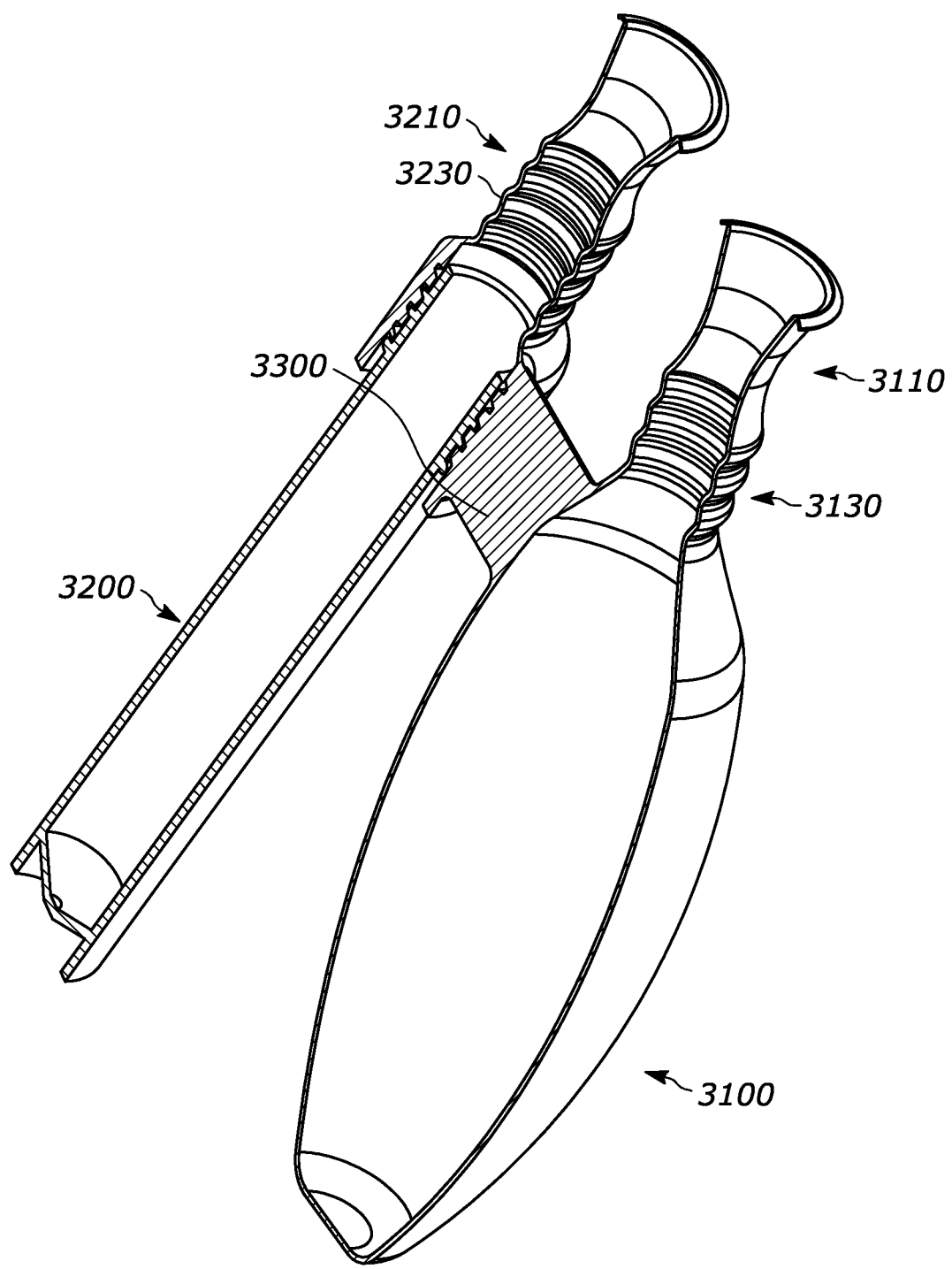

FIGS. 17 and 18 show a fourth example configuration where elements of the dispensing component 3100 and collecting component 3200 are integrally molded together with a connecting bridge 3300 and where alternative, integrally molded nostril interfaces 3110 and 3210 are provided. Nostril interfaces 3110 and 3210 are provided as conical receptacles with a widened mouth for engaging respective patient nostrils as well as undulating or serpentine sections 3130 and 3230 for permitting adjustment of the fit of the respective nostril interfaces.

Figure 19:
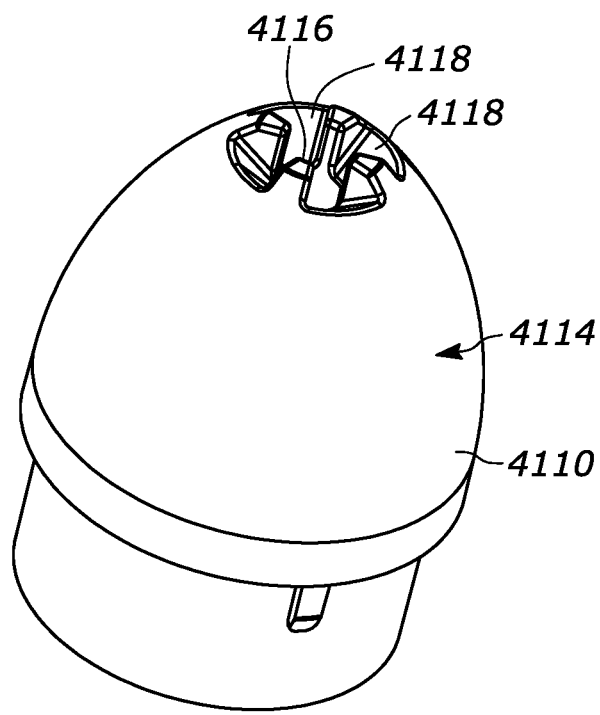
Figure 20:
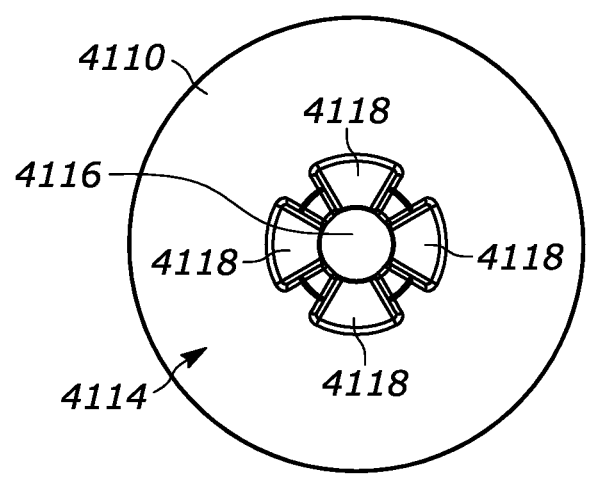
Figure 21:
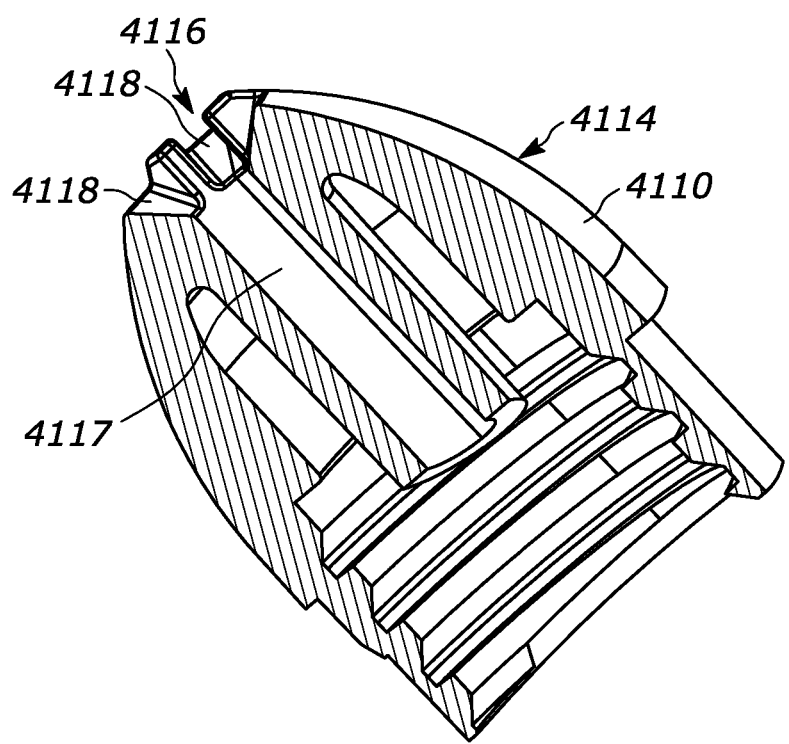

FIGS. 19-21 illustrate an alternative configuration for a nostril engagement tip 4110, which may have a tapered, conical or spherical outer surface 4114 and may be suitable for use with the dispensing component configuration shown in FIGS. 1-10. In this example configuration, the collection wells 118 of the example of FIGS. 1-10 have been replaced with ramped recesses 4118 arranged around a central dispensing port 4116. The ramped recesses 4118 function to collect any stray fluid and return it through the dispensing port 4116 and through passage 4117 to the interior of the pump reservoir. The ramped recesses 4118 may be particularly effective in conjunction with a vacuum developed in the interior of the pump reservoir (i.e., owing to its shape memory) and may thus enhance the collection capabilities of the nostril engagement tip 4110.

Example methods supported by the above-described kits, devices and systems will now be described. A user may assemble the example device shown in FIGS. 1-10 by first obtaining a sealed pump reservoir 102 having a supply of rinsing fluid therein, sealed with a foil seal (i.e., 111 in FIG. 3). The housing 330 may be installed on the shoulder 105 of the pump reservoir 102 and then the nostril engagement tip 110 threaded onto the threaded neck 104, thereby piercing the foil seal with the tapered drop tube mount 118. Reduced diameter portion 112 is located within the housing ring 310. As will be understood, the drop tube 120 may be installed by removing the nostril engagement tip 110 and feeding the drop tube through the now punctured foil seal 111. Installation of the nostril engagement tip 110 also secures the ring 310 of housing 300 to the dispensing component 100. Following installation of the dispensing component 100 to the housing 300, the collecting component 200 may then be assembled to the housing 300. Reduced diameter portion 212 of collecting component nostril engagement tip 210 is inserted into the housing ring 320. Threaded end 204 of collection tube 202 is threaded into the internal threads on the nostril engagement tip 210, thereby retaining the collection tube 202 to the assembly. Absorbent shield 400 is then installed such that cutouts 406 and 408 are positioned around the nostril engagement tips 110 and 210, respectively. The device is now ready for use to obtain a nasopharyngeal sample.

Methods of use may involve the general steps of positioning the dispensing component nostril tip 110 in a first patient nostril, positioning the collecting component nostril tip 120 in a second patient nostril, pressurizing the dispensing component and thereby expelling a stream of rinsing fluid from the dispensing component 110 through the dispensing component nostril interface 110 the into a patient's nostril, nasal cavity and nasopharynx, and collecting effluent from a patient's nostril with the collecting component via the collecting component nostril interface into the collection tube 202. The methods may also include the step of creating a vacuum in the dispensing component bulb reservoir 102 to collect excess rinsing fluid and/or effluent. The methods may further include collecting excess rinsing fluid and/or effluent in collection reservoirs or ramps in one or both of the nostril engagement tips 110 and 210 and collecting excess rinsing fluid and/or effluent by absorption into the shield 400.

Although the present implementations have been described with reference to specific example embodiments, it will be evident that various modifications and changes may be made to these embodiments without departing from the broader spirit and scope of the invention as set forth in the claims. Accordingly, the specification and drawings are to be regarded in an illustrative rather than a restrictive sense.

What is claimed is:

1. A kit for collecting a sample of nasopharyngeal fluid comprising:
   a rinsing fluid supply component comprising: a flexible reservoir pump having an interior for containing a supply of rinsing fluid; a rinsing fluid delivery conduit extending from the reservoir and having a delivery conduit flow passage therein; and a first nostril interface disposed on the delivery conduit and adapted to engage a first nostril of a patient;
   a collecting component, the collecting component comprising: a collection container interface for receiving a collection container; a collection conduit extending to the collection interface; and a second nostril interface disposed on the collection conduit and adapted to engage a second nostril of a patient; and
   an absorbent shield for absorbing stray fluid, wherein the absorbent shield is provided with respective cutouts for receiving the first nostril interface and the second nostril interface.

2. The kit of claim 1, further comprising a housing for supporting the rinsing fluid supply component and the rinsing fluid collecting component, wherein the rinsing fluid supply component is adapted to be secured to the housing and the rinsing fluid supply component is adapted to be secured to the housing.

3. The kit of claim 2, wherein the housing comprises a flexible bridge that is adapted to flex to permit adjustment of the relative positions of the first and second nostril interfaces.

4. The kit of claim 1, wherein at least one of the first and second nostril interfaces comprise an absorbent foam.

5. The kit of claim 1, wherein the flexible reservoir is adapted to resiliently revert to a resting shape so as to permit a user to utilize the flexible reservoir as a vacuum source.

6. The kit of claim 1, wherein at least one of the collection container interface is adapted to receive a standard autosampler vial.

7. The kit of claim 1, wherein at least one of the first and second nostril interfaces comprise a tapered plug.

8. The kit of claim 1, wherein the delivery conduit comprises a drop tube that extends to a bottom portion of the reservoir.

9. The kit of claim 1, wherein the collecting component includes a one-way valve.

10. The kit of claim 1, wherein at least one of the rinsing fluid delivery conduit and collection conduit comprise a flexible section adapted to permit adjustment of the relative positions of the first and second nostril interfaces.

11. The kit of claim 1, wherein the collecting component includes at least one venting passage.

12. The kit of claim 1, wherein the first nostril interface includes at least one collection well or reservoir.

13. The kit of claim 1, wherein the second nostril interface includes at least one collection passage.

14. The kit of claim 1, further comprising a bridge connecting the dispensing component and the collecting component, wherein the flexible reservoir pump and collection container interface are formed integrally with the bridge as a unitary piece.

15. The kit of claim 1, wherein the flexible reservoir includes a frangible seal thereon and wherein the first nostril interface is adapted to be installed on the flexible reservoir and includes an element arranged to pierce the frangible seal when the first nostril interface is installed on the flexible reservoir.

16. The kit of claim 1, wherein the second nostril interface includes at least one venting passage, wherein the at least one venting passage is arranged to be blocked by the absorbent shield when the absorbent shield is in an installed position.

17. A device for collecting a sample of nasopharyngeal fluid comprising:
a rinsing fluid supply component comprising: a flexible reservoir pump having an interior for containing a supply of rinsing fluid; a rinsing fluid delivery conduit extending from the reservoir and having a delivery conduit flow passage therein; and a first nostril interface disposed on the delivery conduit and adapted to engage a first nostril of a patient;
a collecting component, the collecting component comprising: a collection container interface for receiving a collection container; a collection conduit extending to the collection interface; and a second nostril interface disposed on the collection conduit and adapted to engage a second nostril of a patient;
a housing connecting the rinsing fluid supply component and the collecting component; and
an absorbent shield for absorbing stray fluid, wherein the absorbent shield is provided with respective cutouts for receiving the first nostril interface and the second nostril interface.

18. A method collecting a sample of nasopharyngeal fluid comprising:
providing a rinsing fluid supply component comprising: a flexible bulb-shaped reservoir having an interior for containing a supply of rinsing fluid; a rinsing fluid delivery conduit extending from the reservoir and having a delivery conduit flow passage therein; and a first nostril interface disposed on the delivery conduit and adapted to engage a first nostril of a patient;
providing a rinsing fluid collecting component adapted to be secured to the housing the rinsing fluid collecting component comprising: a collection container interface for receiving a collection container; a collection conduit extending to the collection interface; and a second nostril interface disposed on the collection conduit and adapted to engage a second nostril of a patient;
providing an absorbent shield for absorbing stray fluid, wherein the absorbent shield is provided with respective cutouts for receiving the first nostril interface and the second nostril interface;
supplying rinsing fluid from the rinsing fluid supply component through the first nostril interface and into a first nostril and into a nasopharyngeal cavity of a patient; and
collecting rinsing fluid from the nasopharyngeal cavity of the patient with the rinsing fluid collecting component.

19. A kit for collecting a sample of nasopharyngeal fluid comprising:
a rinsing fluid supply component comprising: a flexible reservoir pump having an interior for containing a supply of rinsing fluid; a rinsing fluid delivery conduit extending from the flexible reservoir and having a delivery conduit flow passage therein; and a first nostril interface disposed on the delivery conduit and adapted to engage a first nostril of a patient;
a collecting component, the collecting component comprising: a collection container interface for receiving a collection container; a collection conduit extending to the collection interface; and a second nostril interface disposed on the collection conduit and adapted to engage a second nostril of a patient;
wherein the flexible reservoir includes a frangible seal thereon and wherein the first nostril interface is adapted to be installed on the flexible reservoir and includes an element arranged to pierce the frangible seal when the first nostril interface is installed on the flexible reservoir.

* * * * *